US00PP20641P2

(12) United States Plant Patent
Keogh

(10) Patent No.: US PP20,641 P2
(45) Date of Patent: Jan. 12, 2010

(54) ***CUPHEA* PLANT NAMED 'BALLISTIC'**

(50) Latin Name: *Cuphea×hybrida*
Varietal Denomination: Ballistic

(76) Inventor: Terence Keogh, 209 Bunker Road, Victoria Pt. 4165 Q. (AU)

( * ) Notice: Subject to any disclaimer, the term of this patent is extended or adjusted under 35 U.S.C. 154(b) by 0 days.

(21) Appl. No.: 12/287,628

(22) Filed: Oct. 10, 2008

Related U.S. Application Data

(60) Provisional application No. 61/000,631, filed on Oct. 25, 2007.

(51) Int. Cl.
*A01H 5/00* (2006.01)

(52) U.S. Cl. ..... Plt./420
(58) Field of Classification Search ..... Plt./420
See application file for complete search history.

(56) References Cited

U.S. PATENT DOCUMENTS

PP20,000 P2 * 5/2009 Unger ..... Plt./420

* cited by examiner

*Primary Examiner*—Wendy C. Haas

(57) ABSTRACT

A new and distinct cultivar of *Cuphea* named 'BALLISTIC' that is characterized by mounding habit and many large flowers which are colored pink to red, dark purple and white. In combination these characteristics set 'BALLISTIC' apart from all other existing varieties of *Cuphea* known to the inventor.

2 Drawing Sheets

Botanical designation: *Cuphea ignea×C. lanceolata.*
Denomination: 'BALLISTIC'.

BACKGROUND OF THE INVENTION

The present invention relates to a new and distinct cultivar of *Cuphea* grown as an ornamental plant for garden and landscape. The new invention from the family Lythraceae is known botanically as *Cuphea ignea×C. lanceolata* and will be referred to hereinafter by the cultivar name 'BALLISTIC'.

'BALLISTIC' is a new hybrid plant that resulted from the inventor's deliberate controlled cross-pollination of *Cuphea ignea* and *Cuphea lanceolata.* 'BALLISTIC' is part of a breeding program that commenced in 2002, with the goal of producing a wide variety of ornamental *Cuphea.* In Victoria Point, Queensland, Australia the breeder emasculated flowers of *Cuphea ignea* and secured pollen from *Cuphea lanceolata,* which was then applied to the stigma of the *Cuphea ignea* flowers. Resulting seed was germinated and planted out by the inventor at the inventor's nursery in Queensland, Australia. The inventor selected 'BALLISTIC' from the resulting progeny in 2005. Selection was based on the criteria of quantity, size, and color of flower.

The female parent is an individual *Cuphea ignea* (unpatented) and the male parent is an individual *Cuphea lanceolata* (unpatented). 'BALLISTIC' is distinguishable from the parents by quantity, size, and color of flower. The closest comparison plant is *Cuphea ignea* known commonly as cigar plant. 'BALLISTIC' is distinguishable from the comparison plant by flower color and flower size.

The distinguishing characteristics of 'BALLISTIC' include mounding habit, large flower, many flowers per stem, green foliage, and pink to red, dark purple and white flower color. Flowers bloom throughout the year when kept frost-free and unshaded. Dimensions the first year are 20 cm. in height and 40 cm. in width. Mature dimensions are 60 cm. in height and 60 cm. in width. Cultural requirements include full sun to partial shade, regular soil, and regular water. 'BALLISTIC' is asexually propagated by the method of vegetative cuttings. 'BALLISTIC' is hardy to USDA Zone 9.

The first asexual propagation of 'BALLISTIC' was conducted by the inventor at the inventor's nursery in Queensland, Australia. Asexual propagation was accomplished by the inventor, in 2005. The method used was vegetative cuttings. Since that time under careful observation 'BALLISTIC' has been determined stable, uniform, and true to type in subsequent generations of asexual propagation.

SUMMARY OF THE INVENTION

The following traits have been repeatedly observed and represent the distinguishing characteristics of the new *Cuphea* cultivar named 'BALLISTIC'. These traits in combination set 'BALLISTIC' apart from all other existing varieties of *Cuphea* known to the inventor. 'BALLISTIC' has not been tested under all possible conditions and phenotypic differences may be observed with variations in environmental, climatic, and cultural conditions without however any variance in genotype.

1. 'BALLISTIC' bears a large number of flowers with pink to red tubes, dark purple petals, and a white lip. Many flowers are produced on each stem.
2. 'BALLISTIC' blooms continually through the year when grown frost-free and in unshaved conditions.
3. 'BALLISTIC' is compact reaching a height of approximately 20 cm. and a width of 40 cm. in one growing season.
4. 'BALLISTIC' is hardy to USDA Zone 9.

BRIEF DESCRIPTION OF THE DRAWINGS

The accompanying color drawings illustrate the overall appearance of the new *Cuphea* cultivar named 'BALLISTIC' showing the color as true as is reasonably possible to obtain in color reproductions of this type. Color in the drawings may differ from color values cited in the detailed botanical description, which accurately describe the actual color of the new variety 'BALLISTIC'. Each drawings is taken from a one year old plant of 'BALLISTIC' which has been grown from a cutting in a frost-free greenhouse throughout.

The drawing labeled

The drawing labeled

Figure 1:
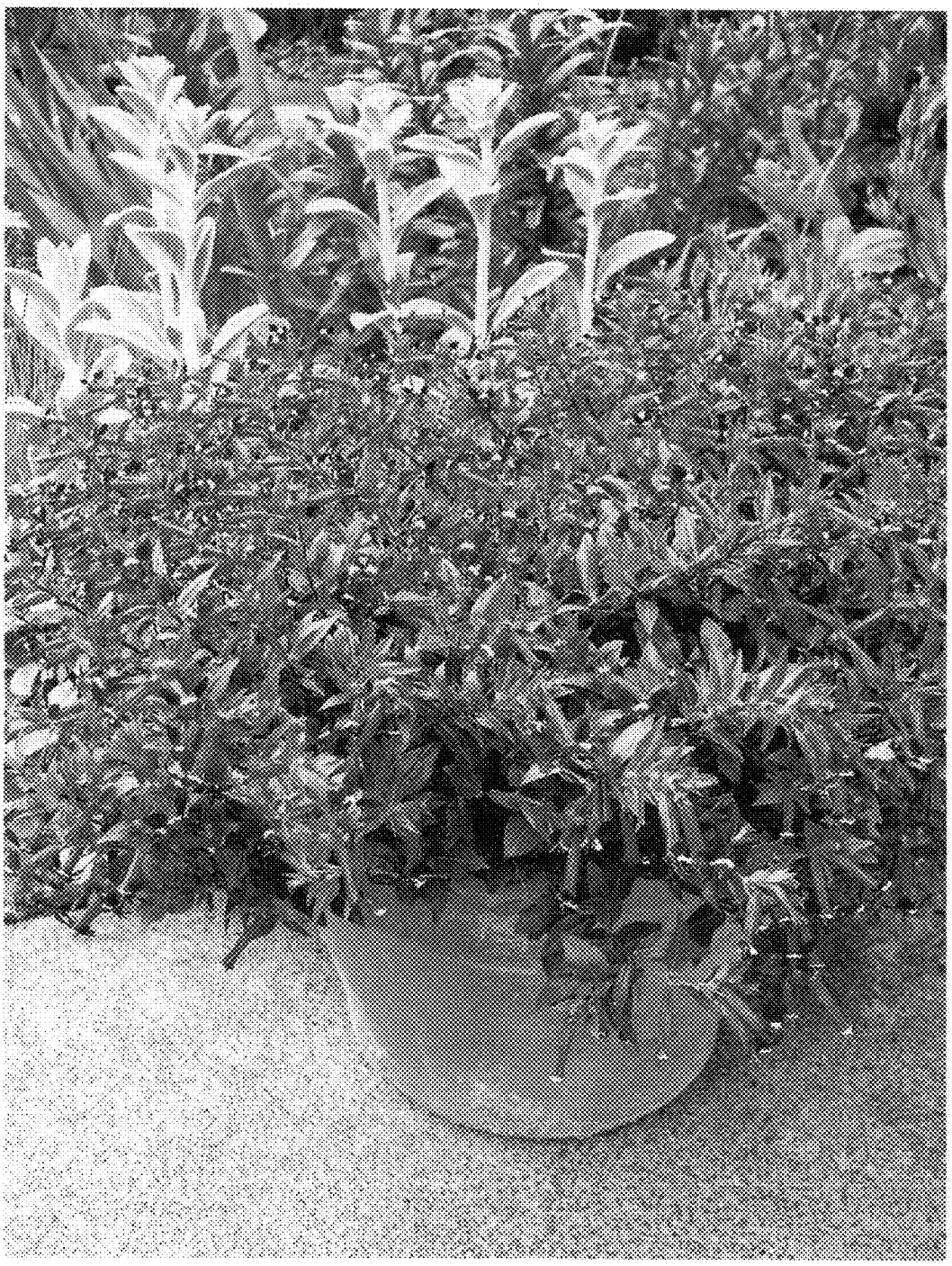
FIG. 1 illustrates a plant of 'BALLISTIC' growing in a container.
Figure 2:
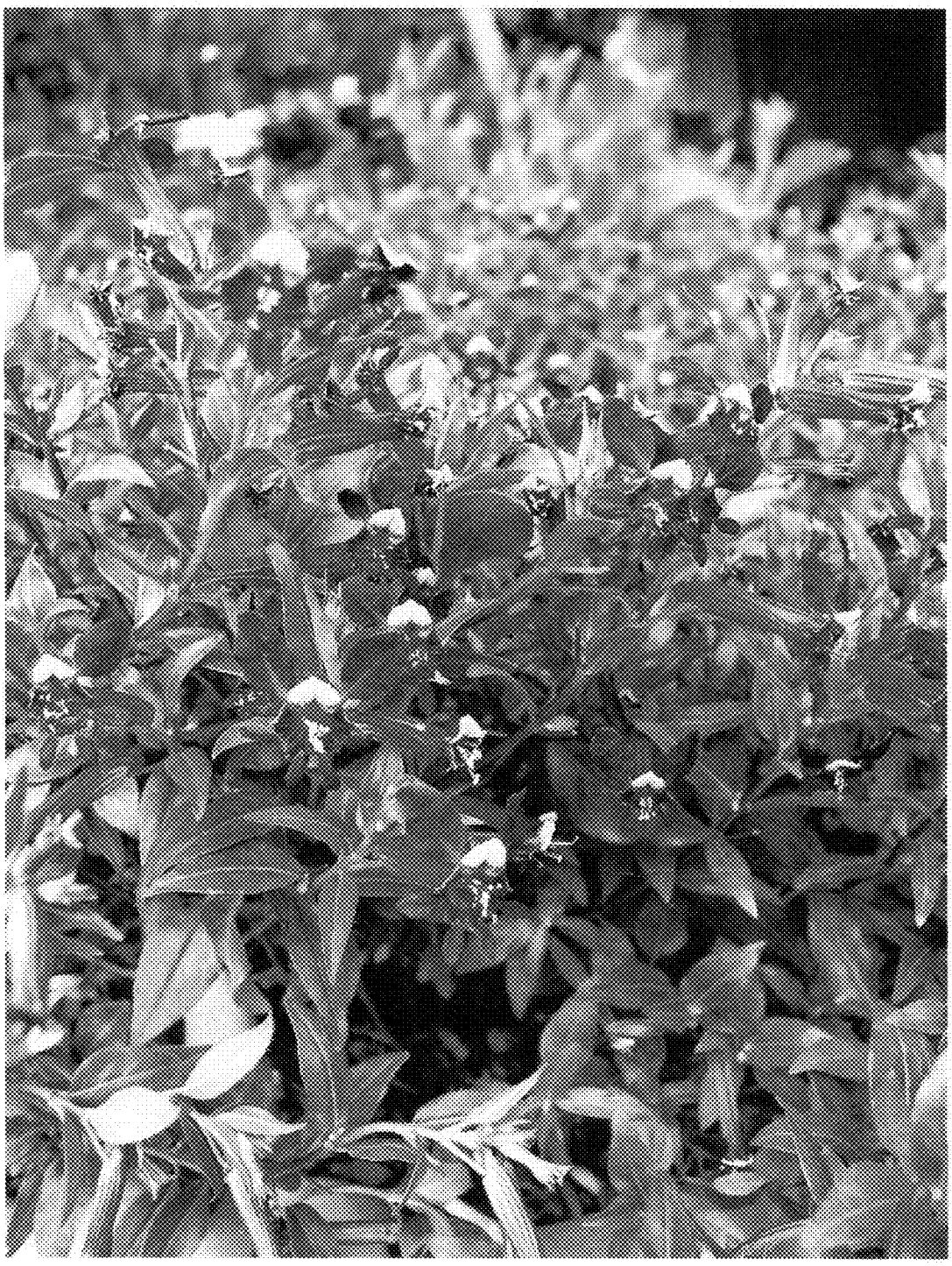
FIG. 2 depicts a close-up view of the flowers on 'BALLISTIC'.

Drawings were made using conventional techniques and although flower and foliage color may appear different from actual color due to light reflectance, they are as accurate as possible by conventional photography.

BOTANICAL DESCRIPTION OF THE PLANT

The following is a detailed botanical description of the new *Cuphea* cultivar named 'BALLISTIC'. Observations, measurements, values and comparisons were collected in Arroyo Grande, Calif., from 9-month-old plants grown under glass and in 1-litre containers. Color determinations are made in accordance with the 2001 Royal Horticultural Society Colour Chart from London, England, except where general color terms of ordinary dictionary significance are used. The growing requirements of the new variety 'BALLISTIC' are similar to the species.

Botanical classification: *Cuphea* ×*hybrida* 'BALLISTIC'.
Family: Lythraceae.
Genus: *Cuphea*.
Species: ×*hybrida*.
Denomination: 'BALLISTIC'.
Common name: Cigar plant.
Habit: Mounding.
Commercial category: Ornamental.
Use: For garden and landscape.
Suggested commercial container size: 1-litre container.
Parentage: *Cuphea* ×*hybrida* 'BALLISTIC' is a hybrid resulting from the deliberate controlled cross-pollination of the following parents:
- *Female parent.*—An individual *Cuphea ignea*.
- *Male parent.*—An individual *Cuphea lanceolata*.

Propagation method: Vegetative cuttings.
Rooting system: Fine.
Vigor: Moderate.
Crop time (range): 6–9 months to produce a 1-litre container from stem cuttings.
Temperature (range): The recommended air temperature is 20–21° Centigrade.
Plant dimensions (first year): 20 cm. in height and 40 cm. in width.
Plant dimensions (at maturity): 60 cm. in height and 60 cm. in width.
Cultural requirements: Grow in full sun to part shade, regular soil, with regular water.
Pest or disease resistance: None known to the inventor.
Pest or disease susceptibility: None known to the inventor.
Hardiness: USDA Zone 9.
Special considerations: Blooms continually throughout the year when kept frost-free and unshaded conditions.

Stem:
- *Shape.*—Cylindrical.
- *Surface.*—Glabrous.
- *Color.*—187A and 165A.
- *Stem length* (*range*).—17–34cm.
- *Stem diameter* (*average*).—3 mm.
- *Internode* (*average*).—1.50 cm.

Foliage:
- *Type.*—Evergreen.
- *Leaf arrangement.*—Opposite.
- *Leaf division.*—Simple.
- *Leaf margin.*—Entire.
- *Leaf surface* (*abaxial and adaxial*).—Glabrous.
- *Leaf shape.*—Ovate.
- *Leaf length* (*average*).—3 cm.
- *Leaf width* (*average*).—1.50 cm.
- *Leaf color* (*abaxial surface*).—138A.
- *Leaf color* (*adaxial surface*).—137A.
- *Leaf apex.*—Acute.
- *Leaf base.*—Aequilateral.
- *Venation.*—Pinnate.
- *Vein color* (*abaxial and adaxial surfaces*).—138D.
- *Attachment.*—Petiolate.
- *Petiole shape.*—Sub-cylindrical.
- *Petiole surface.*—Puberulent.
- *Petiole color.*—165A.
- *Petiole dimensions.*—1 cm. in length and 1 mm. in width.
- *Leaf fragrance.*—None observed.

Inflorescence:
- *Inflorescence* (*axillary and terminal*).—Solitary flower.
- *Quantity* (*average*).—10 per stem.
- *Inflorescence color.*—63A, 61B, 155A, N79A are all individually present.
- *Inflorescence shape.*—Cylindrical and gibbous at base.
- *Aspect.*—Facing upward and outward.
- *Blooming season.*—Year round if frost-free and unshaded.
- *Inflorescence dimensions.*—2 cm. in depth and 1.50 cm. in diameter.
- *Floral tube diameter.*—0.40 cm.
- *Floral tube surface* (*ventral and dorsal*).—Fluted and pubescent.
- *Floral tube color.*—63A, 61B, 155A are individually present.
- *Petals.*—6 sub-equal per inflorescence.
- *Petal shape* (*range*).—Rhombic to ovate.
- *Petal color.*—N79A.
- *Petal margin.*—Entire.
- *Petal surface.*—Glabrous.
- *Petal length* (*range*).—2–6 mm.
- *Petal width* (*range*).—2–3 mm.
- *Petals fused or unfused.*—Unfused.
- *Persistent or self-cleaning.*—Self-cleaning.
- *Peduncle color.*—152A.
- *Peduncle dimensions* (*average*).—0.75 cm. in length and 1 mm. in diameter.
- *Peduncle shape.*—Cylindrical.
- *Peduncle surface.*—Pubescent.
- *Inflorescence fragrance.*—None observed.
- *Lastingness of inflorescence* (*range*).—3–5 days.

Reproductive organs:
- *Stamen quantity.*—10 adnate to floral tube.
- *Stamen length* (*range*).—0.50–0.75 cm.
- *Stamen color.*—N79A.
- *Anther color.*—N79A.
- *Anther length.*—<1 mm.
- *Pollen amount.*—Moderate.
- *Pollen color.*—162B.
- *Pistil quantity.*—1 in number.
- *Pistil length.*—2.50 cm.
- *Pistil color.*—N80D.
- *Stigma dimensions.*—<1 mm. in height and <1 mm. in width.
- *Stigma form.*—Blunt.
- *Stigma color.*—N155A.

*Ovary position.*—Superior.

*Ovary shape.*—Elongated ovoid.

*Ovary dimensions.*—0.75 cm. in height and 0.25 cm. in diameter.

*Ovary color.*—N187D.

What is claimed is:

1. A new and distinct cultivar of *Cuphea* plant named 'BALLISTIC' as described and illustrated herein.

* * * * *